(12) United States Patent
Buelow et al.

(10) Patent No.: US 7,151,090 B2
(45) Date of Patent: *Dec. 19, 2006

(54) METHODS FOR ENHANCING GRAFT SURVIVAL BY MODULATING HEME OXYGENASE ACTIVITY

(75) Inventors: Roland Buelow, Palo Alto, CA (US); Jacky Woo, San Jose, CA (US); Suhasini Iyer, San Ramon, CA (US)

(73) Assignee: Sangstat Medical Corporation, Fremont, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 10/782,260

(22) Filed: Feb. 18, 2004

(65) Prior Publication Data

US 2004/0131602 A1 Jul. 8, 2004

Related U.S. Application Data

(63) Continuation of application No. 09/515,582, filed on Feb. 29, 2000, now Pat. No. 6,861,414, which is a continuation-in-part of application No. PCT/US99/30089, filed on Dec. 17, 1999, and a continuation-in-part of application No. 09/216,005, filed on Dec. 17, 1998, now abandoned.

(51) Int. Cl.
*A61K 31/70* (2006.01)
*A61K 48/00* (2006.01)
*A01N 63/00* (2006.01)

(52) U.S. Cl. .................... 514/44; 424/93.2; 424/93.21; 435/320.1; 435/325; 435/455

(58) Field of Classification Search .................... None
See application file for complete search history.

(56) References Cited

U.S. PATENT DOCUMENTS

| | | | |
|---|---|---|---|
| 4,829,984 A | 5/1989 | Gordon | |
| 5,563,132 A | 10/1996 | Bodaness | |
| 5,756,492 A | 5/1998 | Buelow et al. | |
| 6,013,641 A | 1/2000 | Lussow et al. | |
| 6,060,467 A | 5/2000 | Buelow | |
| 6,861,414 B1 * | 3/2005 | Buelow et al. | 514/44 |

FOREIGN PATENT DOCUMENTS

| | | |
|---|---|---|
| WO | WO 96/09038 A2 | 3/1996 |
| WO | WO 98/09618 A2 | 3/1998 |
| WO | WO 98/09618 A3 | 3/1998 |
| WO | WO 99/23215 A2 | 5/1999 |
| WO | WO 99/23215 A3 | 5/1999 |
| WO | WO 00/12118 A2 | 3/2000 |
| WO | WO 00/12118 A3 | 3/2000 |

OTHER PUBLICATIONS

Blydt-Hansen et al, J Am Soc Nephrol 2003;14:745-54.*
Ke et al, Transplant Proceed 2002 ; 34 :1465-6.*
Christine et al, Am J Transplant 2002 :2:581-92.*
Braudeau et al, Gene Ther 2004 :11 :701-10.*
Abraham, N.G., et al., "Retinal pigment epithelial cell-based gene therapy against hemoglobin toxicity," *Int. J. Mol. Med.* 1:657-663 (1998).
Abraham, N.G., et al., "The physiological significance of heme oxygenase," *Int. J. Biochem.* 20(6):543-558 (1988).
Agarwar, A., et al., "Gas-generating systems in acute renal allograft rejection in the rat," *Transplantation* 61(1):93-98 (Jan. 1996).
Alberts, B., et al., "Chapter 3: Macromolecules: Structure, Shape, and Information," *Molecular Biology of the Cell*, B. Alberts et al. (eds.), 3rd ed., pp. 122-123, Garland Publishing, Inc.: New York, NY (1994).
Amersi, F., et al., "Carbon monoxide provides protection against ischemia/reperfusion injury in rat livers," No. 156, *Conf. Proc. Transplant 2001*, The Joint American Transplant Meeting, Chicago, IL (May 11-16, 2001).
Amersi, R., et al., "Upregulation of heme oxygenase-1 protects genetically fat Zukcer rat livers from ischemia/reperfusion injury," *J. Clin. Invest.* 104(11): 1631-1639 (Dec. 1999).
Arhehali, A., et al., "Direct gene transfer into donor hearts at the time of harvests," *J. Thorac. Cardiovasc. Surg.* 109(4):716-719 (1995).
Bentz, J., et al., "DINAMO: interactive protein alignment and model building," *Bioinformatics* 15(4):309-316 (1999).
Blydt-Hansen, T.D., et al., "Heme oxygenase-1 gene transfer protects against ischemia/reperfusion injury in rat renal isograft model," No. 157, *Conf. Proc. Transplant 2001*, The Joint American Transplant Meeting, Chicago, IL (May 11-16, 2001).
Boasquevisque, C., et al., "*Ex vivo* liposome-mediated gene transfer to lung isografts," *J. Thorac. Cardiovasc. Surg.* 115(1):38-44 (Jan. 1998).
Boucher, R., "Status of gene therapy for cystic fribrosis lung disease," *J. Clin. Invest.* 103(4):441-445 (Feb. 1999).

(Continued)

*Primary Examiner*—Q. Janice Li
(74) *Attorney, Agent, or Firm*—Todd A. Lorenz; Dorsey & Whitney LLP (57) ABSTRACT

Methods are provided wherein the survival of an organ transplant is enhanced by introducing into cells of the transplant a nucleic acid molecule that modulates heme oxygenase-I activity therein. Nucleic acid molecules that modulate heme oxygenase-I activity and therefore find use in the described methods include, for example, molecules that encode a polypeptide that itself exhibits heme oxygenase-I activity or antisense oligonucleotides that act to inhibit heme oxygenase-I activity in a cell.

22 Claims, 3 Drawing Sheets

OTHER PUBLICATIONS

Bowie, J., et al., "Deciphering the Message in Protein Sequences: Tolerance to Amino Acid Substitutions," *Science* 247:1306-1310 (Mar. 1990).

Brauner, R., et al., "Intracoronary adenovirus-mediated transfer of immunosuppressive cytokine genes prolongs allograft survival," *J. Thorac. Cardiovasc. Surg.* 114(6):923-933 (Dec. 1997).

Brouard, S., et al., "Carbon monoxide generated by heme oxygenase-1 suppresses endothelial cell apoptosis through a P38 mark dependent mechanism," No. 1027, *Conf. Proc. Transplant 2001*, The Joint American Transplant Meeting, Chicago, IL (May 11-16, 2001).

Büeler, H., "Adeno-associated viral vectors for gene transfer and gene therapy," *Biol. Chem.* 380(6):613-622 (1999).

Chaveau, C., et al., "Heme oxygenase-1 (HO-1) gene transfer delayed allograft acute rejection in a rat model," No. 36, *Conf. Proc. Transplant 2001*, The Joint American Transplant Meeting, Chicago, IL (May 11-16, 2001).

Coito, A., et al., "Heme oxygenase-1 gene transfer inhibits inducible nitric oxide synthase expression and protects genetically fat Zucker rat livers from ischemia/reperfusion injury," No. 155, *Conf. Proc. Transplant 2001*, The Joint American Transplant Meeting, Chicago, IL (May 11-16, 2001).

Crystal, R.G., "Transfer of genes to humans: early lessons and obstacles to success," *Science* 270(5235):404-410 (Oct. 1995).

Cuturi, M., et al., "RDP1258, a New Rationally Designed Immunosuppressive Peptide, Prolongs Allograft Survival in Rats: Analysis of Its Mechanism of Action," *Mol. Med.* 5(12):820-832 (Dec. 1999).

Dean, p., et al., "Induction of heme oxygenase-1 with cobalt protoporphyrin fails to prolong hamster-to-rat kidney xenograft survival," No. 1266, *Conf. Proc. Transplant 2001*, The Joint American Transplant Meeting, Chicago, IL (May 11-16, 2001).

DeBruyne, L., et al., "Gene transfer of immunomodulatory peptides correlates with heme oxygenase-1 induction and enhanced allograft survival," *Transplantation* 69(1):120-128 (Jan. 2000).

DeBruyne, L., et al., "Lipid-mediated gene transfer of viral IL-10 prolongs vascularized cardiac allograft survival by inhibiting donor-specific cellular and humoral immune response," *Gene Ther.* 5(8):1079-1087 (Aug. 1998).

Drummond, G., et al., "Prevention of neonatal hyperbilirubinemia by tin protoporphyrin IX, a potent competitive inhibitor of heme oxidation," *Proc. Natl. Acad. Sci. USA* 78(10):6466-6470 (Oct. 1981).

Eck, et al., "Chapter 5," *Goodman and Gilman's The Pharmacological Basis of Therapeutics*, 9th ed., pp. 77-101, McGraw Hill: New York, NY (1995).

Evans, C-O, et al., "Cloning and sequencing and expression of cDNA for chick liver heme oxygenase: comparison of avian and mammalian cDNAs and deduced protein," *Biochem. J.* 273:659-666 (1991).

Haga, Y., et al., "Unconjugated bilirubin inhibits *in vitro* major histocompatibility complex-unrestricted cytotoxicity of human lymphocytes," *Biochim. Biophys. Acta* 1316:29-34 (1996).

Hancock, W., et al., "Antibody-induced transplant arteriosclerosis is prevented by graft expression of anti-oxidant and anti-apoptic genes," *Nat. Med.* 4(12):1392-1396 (Dec. 1998).

Hegazy, K.A., et al., "Functional human heme oxygenase has a neuroprotective effect on adult rat ganglion cells after pressure induced ischemia," *NeuroReport* 11(6):1185-1189 (Apr. 2000).

Hori, R., et al., "Gene transfection of H25A mutant heme oxygenase-1 protects cells against hyperoxide-induced cytotoxicity," *J. Biol. Chem.* 277(12):10712-10718 (Mar. 2002).

Ishikawa, K., et al., "Expression of rat heme oxygenase in *Excherichia coli* as a catalytically active, full length form that binds to bacterial membranes," *Eur. J. Biochem.* 202:161-165 (1991).

Iyer, S., et al., "Characterization and biological significance of immunosuppressive peptide D2702.75-84 (E → V) binding protein," *J. Biol. Chem.* 273(5):2692-2697 (1998).

Juan, S-H., et al., "Adenovirus-mediated heme oxygenase-1 gene transfer inhibits the development of atheroscloerosis in apolipoprotein E-deficient mice.* *Circulation* 104:1519-1525 (2001).

Katori, M., et al., "Heme oxygenase-1 overexpression exerts cytoprotective effects against ischemia/reperfusion injury via antiapoptotic pathway," No. 843, *Conf. Proc. Transplant 2001*, The Joint American Transplant Meeting, Chicago, IL (May 11-16, 2001).

Ke, B., et al., "Heme oxygenase-1 gene transfer prevents Fas/Fas ligand-induced apoptosis *in vitro* and improves allograft function *in vivo*," No. 2, *Conf. Proc. Transplant 2001*, The Joint American Transplant Meeting, Chicago, IL (May 11-16, 2001).

Kuemmerle, N.B., et al., "Gene expression after intrarenal injection of plasmid DNA in the rat," *Pediatr. Nephrol.* 14(2):152-157 (2000).

Ledley, F.D., "Pharmaceutical approach to somatic gene therapy," *Pharm. Rev.* 13(11):1595-1614 (Nov. 1996).

Lee, P.J., et al., "Overexpression of heme oxygenase-1 in human pulmonary epithelial cells results in cell growth arrest and increased resistance to hyperoxia," *Proc. Natl. Acad. Sci. USA* 93(19):10393-398 (Sep. 1996).

Lee, R., et al., "Isolated lung liposome-mediated gene transfer produces organ-specific transgenic expression," *Ann. Thorac. Surg.* 66:903-907 (1998).

Levine, F., et al., "Towards gene therapy of diabetes mellitus," *Mol. Med. Today* 5:165-171 (Apr. 1999).

Li, X.K., "Prolonged survival of rat liver allografts transfected with Fas ligand-expressing plasmid," *Transplantation* 66:1416-1423 (1998).

Magee, J.C., et al., "Gene transfer of immunosupressive peptides B2702 and RDP1257 prolongs allograft survival: evidence suggesting a role for heme oxygenase-1," *Transplant. Proc.* 31(1-2):1194-1194 (Feb.-Mar. 1999).

Maines, M., "Zinc protoporphyrin is a selective inhibitor of heme oxygenase activity in the neonatal rat," *Biochim. Biophys. Acta* 673:339-350 (1981).

Marconi, P., et al., "Replication-defective herpes simplex virus for gene therapy *in vivo*," *Proc. Natl. Acad. Sci. USA* 93(21):11319-11320 (Oct. 1996).

Martasek, P., et al., "Properties of human kidney heme oxygenase: inhibition by synthetic heme analogues and matalloporphyrins," *Biochem. Biophys. Res. Commun.* 157(2):480-487 (Dec. 1988).

McClaine, S., et al., "Functional consequences of adenovirus-mediated murine pancreatic gene transfer," *Human Gene Ther.* 8(6):739-746 (Apr. 1997).

Melo, L.G., et al., "Gene therapy strategy for long-term myocardial protection using adeno-associated virus mediated delivery of heme oxygenase gene," *Circulation* 105:602-607 (2002).

Miller, N., et al., "Targeted vectors for gene therapy," *FASEB J.* 9(2):190-199 (Feb. 1995).

Moffatt, S.D., et al., "Comparison between lacrolimus and cyclosporine as immunosuppressive agents compatible with tolerance induction by CD4/CD8 blockade," *Transplantation* 69(8):1724-1726 (Apr. 2000).

Muruve, D., et al., "*Ex vivo* advenovirus-mediated gene therapy leads to long-term expression in pancreatic islet transplants," *Transplantation* 64(3):542-546 (1997).

Nakamura, N., et al., "Early biological effect of *in vivo* gene transfer of platelet-derived growth factor (PDGF)-B into healing patellar ligament," *Gene Ther.* 5(9):1165-1117 (Sep. 1998).

Neil, T.K., et al., "Modulation of corneal heme oxygenase expression by oxidative stress agents," *J. Ocular Pharmacol. Therap.* 11(3):455-468 (1995).

Novogrodsky, A., et al., "Immune stimulatory properties of metalloporphyrins," *J. Immunol.* 143(12):3981-3987 (Dec. 1989).

Omata, Y., et al., "Crystallization and preliminary X-ray diffraction studies on the water soluble from of rat heme oxygenes-1 in complex with heme," *Acta. Cryst.* D54:1017-1019 (1998).

Orkin, S., et al., *Report and Recommendations of the Panel to Assess the NIH Investment in Research on Gene Therapy*, National Institutes of Health: Bethesda, MD (Dec. 1995).

Otterbein, L., et al., "Carbon monoxide has anti-inflammatory effects involving the mitogen-activated protein kinase pathway," *Nat. Med.* 6(4):422-428 (Apr. 2000).

Pileggi, A., et al., "Absence of inducible nitric oxide synthase, and heme oxygenase01 upregulation result in improved islet graft function," No. 833, *Conf. Proc. Transplant 2001*, The Joint American Transplant Meeting, Chicago, IL (May 11-16, 2001).

Qin, L., et al., "Multiple vectors effectively achieve gene transfer in a murine cardiac transplant model," *Transplantation* 59:809-816 (1995).

Qin, L., et al., "Retrovirus-mediated transfer of viral IL-10 gene prolongs murine cardiac allograft survival," *Immunol.* 156:2316-2323 (1996).

Radaelli, C., "Induction of heme oxygenase-1 improves rat liver transplantation survival by inhibiting apoptosis," No. 410, *Conf. Proc. Transplant 2001*, The Joint American Transplant Meeting, Chicago, IL (May 11-16, 2001).

Raju, V., et al., "Coordinated expression and mechanism of induction of HSP32 (heme oxygenase-1) mRNA by hyperthermia in rat organs," *Biochim. Biophys. Acta* 1217:273-280 (1994).

Ribeiro, M., et al., "Inhibition of apoptosis in pancreatic β cells and islets by direct transfer of heme oxygenase-1 protein fused to a protein transduction domain (PTD)," No. 1025, *Conf. Proc. Transplant 2001*, The Joint American Transplant Meeting, Chicago, IL (May 11-16, 2001).

Rotenberg, M.O., et al., "Characterization of a cDNA-encoding rabbit brain heme oxygenase-2 and identification of a conserved domain among mammalian heme oxygenase isozymes: possible heme-binding site," *Arch. Biochem. Biophys.* 290(2):336-344 (Nov. 1991).

Roza, A., et al., "AMD6221, a novel nitric oxide scavenger, decreases heme protein nitrosylation and prolongs cardiac allograft survival," No. 365, *Conf. Proc. Transplant 2001*, The Joint American Transplant Meeting, Chicago, IL (May 11-16, 2001).

Rudinger, J., "Characteristics of the amino acids as components of a peptide hormone sequence," *Peptide Hormones*, pp. 1-7, J.A. Parsons (ed.), University Park Press: Baltimore, MD (1976).

Schmitt, M.P., "Utilization of host iron sources by *Corynebacterium diphtheriae*: identification of a gene whose product is homologous to eukaryotic heme oxygenases and is required for acquisition of iron from heme and hemoglobin," *J. Bact.* 179(5):838-845 (1997).

Schuler, W., et al., "SDZ RAD, a new rapamycin derivative: pharmacological properties *in vitro* and *in vivo*," *Transplantation* 64(1):32-35 (Jul. 1997).

Schuller, D.J., "Crystal structure of heme oxygenase-1," *Nat. Struct. Biol.* 6(9):860-867 (Sep. 1999).

Shaked, A., et al., "Retroviral-mediated gene transfer into rat experimental liver transplant," *Transplantation* 57:32-34 (1994).

Sinal, C.J., et al., "Liver transplantation induces cytochrome P450 1A1 dependent monoxygenase activity in rat lund and kidney," *Can. J. Physiol. Pharmacol.* 73:146-152 (1995).

Soares, M.P., et al., "Expression of heme oxygenase-1 can determine cardiac xenograft survival," *Nat. Med.* 4(9):1073-1077 (Sep. 1998).

Song, Y.K., et al.; "Enhanced gene expression in mouse lung by prolonging the retention time of intravenously injected plasmid DNA," *Gene Ther.* 5(11):1531-1537 91998).

Squiers, E., et al., "Prolongation of porcine islet xenograft survival in mice after therapy with immunosuppressive peptides," *Transplantation* 66(11):1558-1565 (Dec. 1998).

Templeton, N., et al., "New Direction in Liposome Gene Delivery," *Mol. Biotechnol.* 11(2):175-180 (Apr. 1999).

Tenhunen, R., et al., "Microsomal Heme Oxygenase," *J. Biol. Chem.* 244(23):6388-6394 (Dec. 1969).

Verma, I., et al., "Gene therapy—promises, problems and prospects," *Nature* 389(6648):239-242 (Sep. 1997).

Vorburger, S., et al., "Adenoviral Gene Therapy," *Oncologist* 7(1):46-59 (Feb. 2002).

Wang, J., et al., "Adenovirus-mediated gene transfer into rat cardiac allografts," *Transplantation* 61(12):1726-1729 (Jun. 1996).

Wang, N., et al., "Xenograft accomodation: expression of heme oxygenase-1 protects endothelial cells from xenoserum-mediated apoptosis," No. 993, *Conf. Proc. Transplant 2001*, The Joint American Transplant Meeting, Chicago, IL (May 11-16, 2001).

Weiss, G., et al., "Comparative effects of heme and metalloporphyrins on interferon-y-mediated pathways in moncytic cells (THP-1)," *Proc. Soc. Exp. Biol. Med.* 202(4):470-475 (Apr. 1993).

Wilks, A., et al., "Rat liver heme oxygenase: high level expression fo a truncated soluble form and nature of the meso-hydroxylating species," *J. Biol. Chem.* 268(30):22357-22362 (Oct. 1993).

Willis, D., et al., "Heme oxygenase: a novel target for the modulation of the inflammatory response," *Nat. Med.* 2(1):87-90 (Jan. 1996).

Woo, J., et al., "Alleviation of graft-versus-host disease after conditioning with cobalt-protoporphyrin, an inducer of heme oxygenase-1," *Transplantation* 69(4):623-633 (Feb. 2000).

Wringer, E.J., et al., "Antagonizing leukotriene B4 receptors delays cardiac allograft rejection in mice," *Transplantation* 67(6):808-815 (Mar. 1999).

Xia, Q.I., et al., "Production of high tire recombinant aden-associated virsu vectors in the absence of helper adenovirus," *J. Virol.* 72(3):2224:2232 (Mar. 1998).

Yoshida, T., et al., "Human heme oxygenase cDNA and induction of its mRNA by hemin," *Eur. J. Biochem.* 171(3):457-461 (Feb. 1988).

Zhu, N., et al., "Systemic gene expression after intravenous DNA delivery into adult mice," *Science* 261(5118):208-211 (Jul. 1993).

* cited by examiner

```
   1  tcaacgcctg cctcccctcg agcgtcctca gcgcagccgc cgcccgcgga gccagcacga
  61  acgagcccag caccggccgg atggagcgtc cgcaacccga cagcatgccc caggatttgt
 121  cagaggccct gaaggaggcc accaaggagg tgcacaccca ggcagagaat gctgagttca
 181  tgaggaactt tcagaagggc caggtgaccc gagacggctt caagctggtg atggcctccc
 241  tgtaccacat ctatgtggcc ctggaggagg agattgagcg caacaaggag agcccagtct
 301  tcgccctgt ctacttccca gaagagctgc accgcaaggc tgccctggag caggacctgg
 361  ccttctggta cgggcccgc tggcaggagg tcatcccta cacaccagcc atgcagcgct
 421  atgtgaagcg gctccacgag gtggggcgca cagagcccga gctgctggtg gcccacgcct
 481  acacccgcta cctggtgac ctgtctgggg gccaggtgct caaaaagatt gcccagaaag
 541  ccctgacct gcccagctct gcgagggcc tgccttctt cacctttccc aacattgcca
 601  gtgccaccaa gttcaagcag ctctaccgct cccgcatgaa ctccctggag atgactcccg
 661  cagtcaggca gagggtgata gaagaggcca agactgcgtt cctgctcaac atccagctct
 721  ttgaggagtt gcagagctg ctgacccatg acaccaagga ccagagccc tcacggcac
 781  cagggcttcg ccagcgggcc agcaacaaag tgcaagattc tgccccgtg gagactccca
 841  gagggaagcc cccactcaac acccgctccc agctccgct tctccgatgg gtccttacac
 901  tcagctttct ggtggcgaca gttgctgtag ggcttatgc catgtgaatg caggcatgct
 961  ggctcccagg gccatgaact ttgtccggtg gaaggccttc tttctagaga gggaattctc
1021  ttgctggct tcttaccgt gggcactgaa gctttcagg gcctccagcc actttccccg tgggccatgg
1081  gtccctctct ctggaaagga ggaaggagcc tatgcatct tccccaacga aaagcacatc tttttgttgg
1141  caggcaatgg cctaaacttc agaggggcg aagggtcag ccctgcccttt tgttgtgttc tgttgttttt
1201  agttcctgca gcagagcctg gaagacaccc taatgtggca gctgtctcaa cagcatcctc
1261  gccctgagtt tcaagtatcc ttgttgacac ggccatgacc actttccccg tggccatgg
1321  caatttttac acaaacctga aaagatgttg tgtcttgtgt acttttccg tggccatgg
1381  agccactctg ttcctggctc agcctcaaat gcagtatttt tgttgttc tgttgttttt
1441  atagcagggt tgggtgtt tttgagccat tttgtgtgaa gcgtgggtgg ggaggaggt gtttaacggc
1501  actgtggcct tggtctaact tttgtgtgaa ataataaaca acattgtctg
```

METHODS FOR ENHANCING GRAFT SURVIVAL BY MODULATING HEME OXYGENASE ACTIVITY

CROSS-REFERENCES TO RELATED APPLICATIONS

This application is a continuation of U.S. application Ser. No. 09/515,582, filed Feb. 29, 2000, now U.S. Pat. No. 6,861,414, which is a continuation-in-part of U.S. application Ser. No. 09/216,005, filed Dec. 17, 1998, now abandoned, and is a continuation of International Application No. PCT/US99/30089, filed Dec. 17, 1999.

BACKGROUND ART

The inflammatory process is an extraordinarily complex process, varying with the cause of inflammation, the site of the inflammation, and the nature of the insult. Numerous different types of leukocytes are attracted to the site where the inflammatory process is initiated. The different leukocytes initiate different biological processes to respond to the insult. While in many situations, the inflammatory response is healthy in destroying a pathogen, in other situations, such as autoimmune diseases and transplantation, the inflammatory response is undesirable. In the latter case, this leads to rejection and loss of the implanted organ, which in most cases will be fatal.

A number of different avenues have been investigated to encourage the retention of allografts. For the most part, these avenues have involved general immunosuppression, using drugs such as cyclosporin and FK506. Extensive efforts have been directed to inducing anergy toward the foreign tissue. Also, the role of various factors has been investigated, where by modulating the level of those factors, the immune response may be diminished. For the most part, the primary approach has been the use of drugs which suppress the entire immune system, therefore leaving the patient vulnerable to adventitious infection.

Because of the restricted availability of donor organs, consideration has been given to using xenografts for temporary maintenance, while an acceptable allogenic organ is identified. The xenografts not only differ as to the MHC, but will also have numerous other epitopes differing from the host. Therefore, additional rejection mechanisms are brought to bear against the xenograft.

Heme oxygenases (HO) are the rate-limiting enzymes that catalyze the conversion of heme to biliverdin, carbon monoxide (CO) and free iron, the first step in the oxidative conversion of heme to bilirubin. Recently, great interest has been placed on the role of heme oxygenase in cellular responses to stress and insult, including ischemic and immunogenic effects. All of the end products of heme degradation, including biliverdin, bilirubin, and CO, are known to modulate immune effector functions. Biliverdin has also been shown to inhibit human complement in vitro. Bilirubin inhibits human lymphocyte responses, including PHA-induced proliferation, IL-2 production, and antibody-dependent and -independent cell-mediated cytotoxicity. In addition, heme oxygenase-I (HO-1) upregulation correlates with increased production of nitric oxide (NO), an important effector molecule involved in inflammation and immune regulation. On the other hand, NO is also known to induce HO-1 expression, while CO directly inhibits nitric oxide synthase (NOS) activity by binding to the heme moiety of the NOS enzyme and thus downregulating NO production. Like NO, CO contributes to endothelium-dependent vasodilation and inhibits platelet aggregation by elevating intracellular cGMP levels. The deleterious effects of hyperoxia are thought to be mediated by reactive oxygen species. Both biliverdin and bilirubin are efficient peroxyl radical scavengers that inhibit lipid peroxidation. Bilirubin scavenges peroxyl radicals as efficiently as α-tocopherol, which is regarded as the most potent antioxidant of lipid peroxidation. On the other hand, oxygen radicals may trigger cascade of antiapoptotic events, including those that involve activation of bcl-2 protooncogene. All these factors point to a complex picture of putative regulatory interactions between the HO system and the host cytokine network set in motion through the biological activity of heme degradation products.

There is a pressing need to find alternative modalities which will enhance and extend transplant survival. These modalities may find use in conjunction with other drugs, where lower levels of other drugs having significant side effects may be used effectively, to reduce the detrimental side effects. Thus, there is substantial interest in developing new approaches to improving transplant outcome, where a drug may act by itself or in conjunction with other drugs.

BRIEF DESCRIPTION OF THE RELEVANT LITERATURE

Heme oxygenase has been the subject of numerous studies as evidenced by the review article, Abraham et al., *Int. J. Biochem.* 20(6):543–558 (1988). Recently, modulation of heme oxygenase activity has been described in Raju and Maines, *Biochimica et Biophysica Acta* 1217:273–280 (1994); Neil et al., *J. of Ocular Pharmacology and Therapeutics* 11(3):455–468 (1995); Haga et al., ibid., 1316:29–34 (1996); Willis et al., *Nature Medicine* 2(1):87–90 (1996); and Agarwal et al., *Transplantation* 61(1):93–98 (1996).

SUMMARY

In one embodiment of the present invention, methods are provided for extending the survival of an organ transplant in a recipient, wherein those methods comprise contacting the organ transplant with a nucleic acid that functions to modulate heme oxygenase-I activity in those cells, whereby the survival time of the organ transplant in the recipient is extended. In one embodiment, the nucleic acid encodes a heme oxygenase polypeptide.

Yet another embodiment of the present invention is directed to methods for extending the survival of an organ transplant in a recipient, wherein the methods comprise contacting cells of the organ transplant with a nucleic acid encoding a polypeptide having heme oxygenase activity, wherein the nucleic acid is expressed in the cells in an amount sufficient to increase heme oxygenase activity therein, whereby the survival time of the transplant is extended. Additional embodiments will become evident upon a reading of the present specification.

BRIEF DESCRIPTION OF THE DRAWINGS

FIG. 3 shows the nucleic acid sequence (SEQ ID NO:1) of a cDNA encoding human heme oxygenase-I (nucleotides 81–944).

DESCRIPTION OF SPECIFIC EMBODIMENTS

Methods are herein provided for prolonging the survival of transplants in a mammalian host. In a preferred embodiment, the methods comprise contacting cells of the organ transplant with a nucleic acid molecule that functions to modulate heme oxygenase-I (HO-1) activity in cells of the organ transplant, whereby the survival time of the organ transplant in the recipient is extended. For the most part, nucleic acid molecules that function to modulate HO-1 activity in cells will be nucleic acid molecules that encode a polypeptide that exhibits at least one biological activity that is normally associated with the human HO-1 polypeptide encoded by nucleotides 81–944 of the nucleic acid shown in FIG. 3 (SEQ ID NO:1) or will be antisense oligonucleotides whose sequences are derived from and/or based upon nucleotides 81–944 of the human heme oxygenase-I nucleotide sequence shown in FIG. 3 (SEQ ID NO:1) or non-coding sequences of a heme oxygenase-encoding nucleic acid molecule.

By "heme oxygenase-I", "HO-1" and grammatical equivalents thereof is meant the polypeptide encoded by nucleotides 81–944 of the nucleotide sequence shown in FIG. 3 (SEQ ID NO:1) and homologs thereof which exhibit at least one biological activity that is normally associated with the human heme oxygenase-I enzyme. Preferably, the heme oxygenase-I activity exhibited by the polypeptides is the ability to catalyze the first step in the oxidative degradation of heme to bilirubin (Tenhunen et al., *J. Biol. Chem.* 244:6388–6394 (1969) and Tenhunen et al., *J. Lab. Clin. Med.* 75:410–421 (1970)). In this regard, Applicants note that quick, easy and reliable assays are known in the art to determine whether a polypeptide exhibits heme oxygenase-I activity, wherein those assays may be routinely employed to test the ability of any polypeptide for the presence of heme oxygenase-I activity. For example, the production of bilirubin from heme can be determined using a spectrophotometer, whereby the increase in optical density at 468 mμ in a mixture of the peptide, hemin, biliverdin reductase and NADPH indicates heme oxygenase activity.

The terms "polypeptide" and "protein" may be used interchangeably throughout this application and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

Also encompassed by "heme oxygenase-I", "HO-1", etc. are homolog polypeptides having at least about 80% sequence identity, usually at least about 85% sequence identity, preferably at least about 90% sequence identity, more preferably at least about 95% sequence identity and most preferably at least about 98% sequence identity with the polypeptide encoded by nucleotides 81–944 of the nucleotide sequence shown in FIG. 3 (SEQ ID NO:1) and which exhibit at least one biological activity that is normally associated with the human heme oxygenase-I enzyme.

By "nucleic acid molecules that encode NO-1", "nucleic acid molecules encoding a polypeptide having heme oxygenase-I activity" and grammatical equivalents thereof is meant the nucleotide sequence of human heme oxygenase-I as shown nucleotides 81–944 of FIG. 3 (SEQ ID NO:1) as well as nucleotide sequences having at least about 80% sequence identity, usually at least about 85% sequence identity, preferably at least about 90% sequence identity, more preferably at least about 95% sequence identity and most preferably at least about 98% sequence identity with nucleotides 81–944 of the nucleotide sequence shown in FIG. 3 (SEQ ID NO:1) and which encode a polypeptide that exhibits at least one biological activity that is normally associated with the human heme oxygenase-I enzyme.

As is known in the art, a number of different programs can be used to identify whether a protein or nucleic acid has sequence identity or similarity to a known sequence. Sequence identity and/or similarity is determined using standard techniques known in the art, including, but not limited to, the local sequence identity algorithm of Smith & Waterman, *Adv. Appl. Math.* 2:482 (1981), by the sequence identity alignment algorithm of Needleman and Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucleic Acids Res.* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," *Macromolecule Sequencing and Synthesis, Selected Methods and Applications*, pp 127–149, Alan R. Liss, Inc. (1988).

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, *J. Mol. Evol.* 35:351–360 (1987); the method is similar to that described by Higgins and Sharp, *CABIOS* 5:151–153 (1989). Useful PILEUP parameters including a default gap weight of 3.00, a default gap length weight of 0.10, and weighted end gaps.

Another example of a useful algorithm is the BLAST algorithm, described in Altschul et al., *J. Mol. Biol.* 215: 403–410, (1990) and Karlin et al., *Proc. Natl. Acad. Sci. USA* 90:5873–5787 (1993). A particularly useful BLAST program is the WU-BLAST-2 program which was obtained from Altschul et al., *Methods in Enzymology* 266:460–480 (1996) (available at world wide web site blast.wust/edu/blast/README.html). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent (%) amino acid or nucleic acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the amino acid sequence of the polypeptide encoded by nucleotides 81–944 of the nucleotide sequence shown in FIG. 3 (SEQ ID NO:1), it is understood that in one embodiment, the percentage of sequence identity will be determined based on the number of identical amino acids in relation to the total number of amino acids. Thus, for example, sequence identity of sequences shorter than that of the polypeptide encoded by nucleotides 81–944 of the nucleotide sequence shown in FIG. 3 (SEQ ID NO:1), as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Heme oxygenase-I having less than 100% sequence identity with the polypeptide encoded by nucleotides 81–944 of the nucleotide sequence shown in FIG. 3 (SEQ ID NO:1) will generally be produced from native heme oxygenase-I nucleotide sequences from species other than human and variants of native heme oxygenase-I nucleotide sequences from human or non-human sources. In this regard, it is noted that many techniques are well known in the art and may be routinely employed to produce nucleotide sequence variants of native heme oxygenase-I sequences and assaying the polypeptide products of those variants for the presence of at least one activity that is normally associated with a native heme oxygenase-I polypeptide.

Polypeptides having heme oxygenase-I activity may be shorter or longer than the polypeptide encoded by nucleotides 81–944 of the nucleotide sequence shown in FIG. 3 (SEQ ID NO:1). Thus, in a preferred embodiment, included within the definition of heme oxygenase-I polypeptide are portions or fragments of the polypeptide encoded by nucleotides 81–944 of the nucleotide sequence shown in FIG. 3 (SEQ ID NO:1). In one embodiment herein, fragments of the polypeptide encoded by nucleotides 81–944 of the nucleotide sequence shown in FIG. 3 (SEQ ID NO:1) are considered heme oxygenase-I polypeptides if a) they have at least the indicated sequence identity; and b) preferably have a biological activity of naturally occurring heme oxygenase-I, as described above.

In addition, as is more fully outlined below, heme oxygenase-I can be made longer than the polypeptide encoded by nucleotides 81–944 of the nucleotide sequence shown in FIG. 3 (SEQ ID NO:1); for example, by the addition of other fusion sequences, or the elucidation of additional coding and non-coding sequences.

The heme oxygenase-I polypeptides are preferably recombinant. A "recombinant polypeptide" is a polypeptide made using recombinant techniques, i.e., through the expression of a recombinant nucleic acid as described below. In a preferred embodiment, the heme oxygenase-I of the invention is made through the expression of nucleotides 81–944 of the nucleotide sequence shown in FIG. 3 (SEQ ID NO:1), or fragment thereof. A recombinant polypeptide is distinguished from naturally occurring protein by at least one or more characteristics. For example, the polypeptide may be isolated or purified away from some or all of the proteins and compounds with which it is normally associated in its wild type host, and thus may be substantially pure. For example, an isolated polypeptide is unaccompanied by at least some of the material with which it is normally associated in its natural state, preferably constituting at least about 0.5%, more preferably at least about 5% by weight of the total protein in a given sample. A substantially pure polypeptide comprises at least about 75% by weight of the total polypeptide, with at least about 80% being preferred, and at least about 90% being particularly preferred. The definition includes the production of a heme oxygenase-I polypeptide from one organism in a different organism or host cell. Alternatively, the polypeptide may be made at a significantly higher concentration than is normally seen, through the use of an inducible promoter or high expression promoter, such that the polypeptide is made at increased concentration levels. Alternatively, the polypeptide may be in a form not normally found in nature, as in the addition of amino acid substitutions, insertions and deletions, as discussed below.

As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in FIGS. 1 and 3 also include the complement of the sequence. By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

In one embodiment, the present invention provides nucleic acids encoding heme oxygenase-I variants. These variants fall into one or more of three classes: substitutional, insertional or deletional variants. These variants ordinarily are prepared by site specific mutagenesis of nucleotides in nucleotides 81–944 of the nucleic acid shown in FIG. 3 (SEQ ID NO:1), using cassette or PCR mutagenesis or other techniques well known in the art, to produce DNA encoding the variant, and thereafter expressing the DNA in a transplant graft, as described below, or a recombinant cell culture as outlined above. Amino acid sequence variants are characterized by the predetermined nature of the variation, a feature that sets them apart from naturally occurring allelic or interspecies variation of the heme oxygenase-I amino acid sequence. The variants typically exhibit the same qualitative biological activity as the naturally occurring analogue, although variants can also be selected which have modified characteristics as will be more fully outlined below.

While the site or region for introducing a sequence variation is predetermined, the mutation per se need not be predetermined. For example, in order to optimize the performance of a mutation at a given site, random mutagenesis may be conducted at the target codon or region and the expressed variants screened for the optimal desired activity. Techniques for making substitution mutations at predetermined sites in DNA having a known sequence are well known, for example, M13 primer mutagenesis and PCR mutagenesis. Another example of a technique for making variants is the method of gene shuffling, whereby fragments of similar variants of a nucleotide sequence are allowed to recombine to produce new variant combinations. Examples of such techniques are found in U.S. Pat. Nos. 5,605,703; 5,811,238; 5,873,458; 5,830,696; 5,939,250; 5,763,239; 5,965,408; and 5,945,325, each of which is incorporated by reference herein in its entirety. Screening of the mutants is done using assays of heme oxygenase activities, as described above.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the heme oxygenase-I are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally occurring analogue, although variants also are selected to modify the characteristics of the heme oxygenase-I as needed. Alternatively, the variant may be designed such that the biological activity of the protein is altered.

One type of covalent modification of a polypeptide included within the scope of this invention comprises altering the native glycosylation pattern of the polypeptide. "Altering the native glycosylation pattern" is intended for purposes herein to mean deleting one or more carbohydrate moieties found in native sequence heme oxygenase-I polypeptide, and/or adding one or more glycosylation sites that are not present in the native sequence polypeptide.

Addition of glycosylation sites to polypeptides may be accomplished by altering the amino acid sequence thereof. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Removal of carbohydrate moieties present on the polypeptide may be accomplished by mutational substitution of codons encoding for amino acid residues that serve as targets for glycosylation.

To produce HO-1 protein to test for heme oxygenase activity, heme oxygenase-I is cloned and expressed as outlined below. Thus, probe or degenerate polymerase chain reaction (PCR) primer sequences may be used to find other related heme oxygenase-I polypeptides from humans or other organisms. As will be appreciated by those in the art, particularly useful probe and/or PCR primer sequences include the unique areas of the nucleic acid sequence shown in FIG. 3 (SEQ ID NO:1). As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences provided herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant nucleic acid can be further-used as a probe to identify and isolate other nucleic acids. It can also be used as a "precursor" nucleic acid to make modified or variant nucleic acids and proteins.

Using the nucleic acids of the present invention which encode a protein, a variety of expression vectors can be made. The expression vectors may be either self-replicating extrachromosomal vectors or vectors which integrate into a host genome. Generally, these expression vectors include transcriptional and translational regulatory nucleic acid operably linked to the nucleic acid encoding the protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the heme oxygenase-I; for example, transcriptional and translational regulatory nucleic acid sequences from Bacillus are preferably used to express the heme oxygenase-I in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in WO 97/27212 and WO 97/27213, both of which are hereby expressly incorporated by reference.

Proteins of the present invention are produced by culturing a host cell transformed with an expression vector containing nucleic acid encoding the protein, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector may require optimizing the growth and proliferation of the host cell, while the use of an inducible promoter requires the appropriate conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are Drosophila melanogaster cells, Saccharomyces cerevisiae and other yeasts, E. coli, Bacillus subtilis, SF9 cells, C129 cells, 293 cells, Neurospora, BHK, CHO, COS, and HeLa cells, fibroblasts, Schwanoma cell lines, immortalized mammalian myeloid and lymphoid cell lines, tumor cell lines, and B lymphocytes.

In a preferred embodiment, the proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for a protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Proteins may be expressed in bacterial systems. Bacterial expression systems are well known in the art.

A suitable bacterial promoter is any nucleic acid sequence capable of binding bacterial RNA polymerase and initiating the downstream (3') transcription of the coding sequence of cell cycle protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli.*, the ribosome binding site is called the Shine-Delgamo (SD) sequence and includes an initiation codon and a sequence 3–9 nucleotides in length located 3–11 nucleotides upstream of the initiation codon.

The expression vector may also include a signal peptide sequence that provides for secretion of the protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

Proteins may be produced in insect cells. Expression vectors for the transformation of insect cells, and in particular, baculovirus-based expression vectors, are well known in the art.

Proteins may also be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The protein may also be made as a fusion protein, using techniques well known in the art. Thus, for example, the protein may be made as a fusion protein to increase expression, or for other reasons. For example, when the protein is a peptide, the nucleic acid encoding the peptide may be linked to other nucleic acid for expression purposes.

To test for heme oxygenase activity, the protein is purified or isolated after expression. Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the heme oxygenase protein may be purified using a standard anti-heme oxygenase antibody column. Ultrafiltration and diafiltration techniques, in conjunction with protein concentration, are also useful. For general guidance in suitable purification techniques, see Scopes, R., *Protein Purification*, Springer-Verlag, NY (1982). The degree of purification necessary will vary depending on the use of the heme oxygenase-I protein. In some instances no purification will be necessary.

Nucleic acid molecules encoding heme oxygenase-I as well as any nucleic acid molecule derived from either the coding or non-coding strand of a nucleic acid molecule that encodes heme oxygenase-I may be contacted with cells of a organ transplant in a variety of ways which are known and routinely employed in the art, wherein the contacting may be ex vivo or in vivo. The particular protocol will depend upon the nature of the organ, the form of the nucleic acid, and the use of immunosuppressants or other drugs.

By the term "conditions permissive for the contacting of exogenous nucleic acid", and grammatical equivalents herein is meant conditions which allow cells of the ex vivo or in vivo organ transplant to be contacted with the exogenous nucleic acid, whereby heme oxygenase activity is modified. In a preferred embodiment, contacting results in the uptake of the nucleic acid into the cells.

In a preferred embodiment, the nucleic acid encodes a protein which is expressed. In some embodiments, the expression of the exogeneous nucleic acid is transient; that is, the exogeneous protein is expressed for a limited time. In other embodiments, the expression is permanent In some embodiments, the exogeneous nucleic acid is incorporated into the genome of the target cell; for example, retroviral vectors described below integrate into the genome of the host cell. Generally this is done when longer or permanent expression is desired. In other embodiments, the exogeneous nucleic acid does not incorporate into the genome of the target cell but rather exists autonomously in the cell; for example, many such plasmids are known. This embodiment may be preferable when transient expression is desired.

The permissive conditions will depend on the form of the exogenous nucleic acid. The production of various expression vectors is described above. Thus, for example, when the exogenous nucleic acid is in the form of an adenoviral, retroviral, or adeno-associated viral vector, the permissive conditions are those which allow viral contact and/or infection of the cell. Similarly, when the exogenous nucleic acid is in the form of a plasmid, the permissive conditions allow the plasmid to contact or enter the cell. Thus, the form of the exogenous nucleic acid and the conditions which are permissive for contacting are correlated. These conditions are generally well known in the art.

Permissive conditions depend on the expression vector to be used, the amount of expression desired and the target cell. Generally, conditions which allow in vitro uptake of exogenous cells work for ex vivo and in vivo cells.

Permissive conditions are analyzed using well-known techniques in the art. For example, the expression of exogenous nucleic acid may be assayed by detecting the presence of mRNA, using Northern hybridization, or protein, using antibodies or biological function assays.

Specific conditions for the uptake of exogenous nucleic acid are well known in the art. They include, but are not limited to, retroviral infection, adenoviral infection, transformation with plasmids, transformation with liposomes containing exogenous nucleic acid, biolistic nucleic acid delivery (i.e., loading the nucleic acid onto gold or other metal particles and shooting or injecting into the cells), adenoassociated virus infection, HIV virus infection and Epstein-Barr virus infection. These may all be considered "expression vectors" for the purposes of the invention.

The expression vectors may be either extrachromosomal vectors or vectors which integrate into a host genome as outlined above. Generally, these expression vectors include transcriptional and translational regulatory nucleic acid operably linked to the exogenous nucleic acid. "Operably linked" in this context means that the transcriptional and translational regulatory DNA is positioned relative to the coding sequence of the exogenous protein in such a manner that transcription is initiated. Generally, this will mean that the promoter and transcriptional initiation or start sequences are positioned 5' to the exogenous protein coding region. The transcriptional and translational regulatory nucleic acid will generally be appropriate to the host cell in which the exogenous protein is expressed; for example, transcriptional and translational regulatory nucleic acid sequences from mammalian cells, and particularly humans, are preferably used to express the exogenous protein in mammals and humans. Numerous types of appropriate expression vectors, and suitable regulatory sequences are known in the art.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive, tissue specific or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

Suitable retroviral vectors include LNL6, LXSN, and LNCX (see Byun et al., *Gene Ther.* 3(9):780–8 (1996) for review).

In a preferred embodiment, the nucleic acids are contacted cells of a transplant organ in the form of an adenovirus. Suitable adenoviral vectors include modifications of human adenoviruses such as Ad2 or Ad5, wherein genetic elements necessary for the virus to replicate in vivo have been removed; e.g., the E1 region, and an expression cassette coding for the exogenous gene of interest inserted into the adenoviral genome (for example $Ad_{GV}CFTR_{10}$).

In one embodiment of the present invention, the nucleic acid molecule is introduced into cells of the organ transplant by liposome-mediated nucleic acid transfer. In this regard, many liposome-based reagents are well known in the art, are commercially available and may be routinely employed for introducing a nucleic acid molecule into cells of the organ transplant. Certain embodiments of the present invention will employ cationic lipid transfer vehicles such as Lipofectamine or Lipofectin (Life Technologies), dioleoylphosphatidylethanolamine (DOPE) together with a cationic cholesterol derivative (DC cholesterol), N[1-(2,3-dioleyloxy)propyl]-N,N,N-trimethylammonium chloride (DOTMA) (Sioud et al., *J. Mol. Biol.* 242:831–835 (1991)), DOSPA:DOPE, DOTAP, DMRIE:cholesterol, DDAB:DOPE, and the like. Production of liposome encapsulated nucleic acid is well known in the art and typically involves the combination of lipid and nucleic acid in a ratio of about 1:1.

In vivo delivery includes, but is not limited to direct injection into the organ, via catheter, or by other means of perfusion. The nucleic acid may be administered intravascularly at a proximal location to the transplant organ or administered systemically. One of ordinary skill in the art will recognize the advantages and disadvantages of each mode of delivery. For instance, direct injection may produce the greatest titer of nucleic acid in the organ, but distribution of the nucleic acid will likely be uneven throughout the organ. Introduction of the nucleic acid proximal to the transplant organ will generally result in greater contact with the cells of the organ, but systemic administration is generally much simpler. Administration may also be to the donor prior to removal of the organ. The nucleic acids may be introduced in a single administration, or several administrations, beginning before removal of the organ from the donor as well as after transplantation. The skilled artisan will be able to determine a satisfactory means of delivery and delivery regimen without undue experimentation.

Nucleic acids may be contacted with cells of the transplant organ ex vivo. When bathing the organ in a composition comprising the nucleic acids, conventional medium may be sued, such as organ preservation solution. The temperature at which the organ may be maintained will be conventional, typically in the range of about 1° to 8° C. The residence time of the organ in the medium will generally be in the range of about 10 minutes to 48 hours, more usually about 10 minutes to 2 hours. The nucleic acids may be contacted with cells of the organ in vivo as well as ex vivo.

In a preferred embodiment, the nucleic acid is contacted with cells of a organ transplant by direct injection into the transplanted organ. In this regard, it is well known in the art that living cells are capable of internalizing and incorporating exogenous nucleic acid molecule with which the cells come in contact. That nucleic acid may then be expressed by the cell that has incorporated it into its nucleus.

In a preferred embodiment, the nucleic acid is contacted with cells of a transplant organ by intravascular injection proximate to the transplant organ. In an alternate preferred embodiment, the nucleic acid is contacted with cells of a transplant organ by systemic administration.

The above described nucleic acid molecules will function to modulate the overall heme oxygenase-I activity of a cell with which it is contacted. In cases where the nucleic acid molecule encodes a polypeptide having at least one activity normally associated with the human heme oxygenase-I polypeptide, the modulation will generally be exemplified by an increase in the heme oxygenase-I activity of the cell in which the nucleic acid molecule is expressed. In cases where the nucleic acid molecule is an antisense heme oxygenase-I oligonucleotide, the modulation will generally be exemplified by a decrease in the heme oxygenase-I activity of the cell into which the nucleic acid molecule is introduced.

The subject nucleic acids may be used with a wide variety of hosts, particularly primates, more particularly humans, or with domestic animals. The subject nucleic acids may be used in conjunction with the transplantation of a wide variety of organs, including, but not limited to, kidney, heart, liver, spleen, bone marrow, pancreas, lung, and islet of langerhans. The subject nucleic acids may be used for allogenic, as well as xenogenic, grafts.

The subject nucleic acids may be used as adjunctive therapy with immunosuppressant compounds, such as cyclosporin, FK506, MHC class I oligopeptides, or other immunosuppressants. Such adjunct use may allow reduced amounts of the immunosuppressant to be used than would be used otherwise.

Generally, the graft life will be extended for a significant amount of time beyond what could normally be anticipated in the absence of the subject nucleic acids, more usually at least five days. The actual amount of time transplant life is extended will vary with the various conditions of the procedure, particularly depending on the organ type to be transplanted. This can be useful in areas where xenogeneic grafts have been used awaiting an allogenic graft, to allow for reduced amounts of immunosuppressants or avoid using immunosuppressants altogether.

EXPERIMENTAL

Example 1

Metalloprotoporphyrin-induced Immunomodulation

Materials and Methods

Animals: Male, 7–8 week old CBA/J (H-$2^k$) and C57BL/6/J (H-$2^b$) mice were purchased from the Jackson Laboratory (Bar Harbor, Me.). Mice were maintained in our animal facility following Animal Welfare Guideline, Department of Health, Calif.

Synthetic Metalloporphyrins: Various synthetic metalloporphyrins were purchased from Porphyrin Products, Inc. (Logan, Utah). They were dissolved in 0.2 M NaOH, adjusted to pH 74 with 1 M HCl and subsequently diluted to 1 mg/ml in PBS.

Cytotoxic T-cell Activity: To assay the effect of metalloprotoporphyrins on cytotoxic T-cell activity, CBA to B6 effectors were generated following a five day culture of $3 \times 10^6$ CBA spleen cells with $3 \times 10^6$ mitomycin-treated B6 spleen cells in wells of a 24-well plate (Nunclone, Delta, Nunc, Denmark) in R-10 medium. Effector cells were then harvested and washed. (H$2^b$), a mouse lymphoma induced in C57BL/6N was used as target cells. EL4 cells were routinely subcultured once every three days. They were then collected, washed, and labeled with 0.1 mCi of sodium chromate-51 in 200 µl for one hour at 37° C. Effector (E) and target (t) cells were added into V-shaped tissue culture plates (Nunc, Denmark) at E:T of 20:1. Metalloprotoporphyrins were diluted to the working concentrations with PBS and added at the beginning of the four hour incubation period. For the determination of maximal release, 1% triton X-100 was added to separate wells. Plates were centrifuged for three minutes to increase cellular contact before the four hour incubation period. After incubation 75 µl supernatant from each well was collected and the amount of $^{51}$Cr released was counted using a TopCount scintillation counter. The degree of cell lysis was calculated using the formula below:

$$\% \text{ lysis} = \frac{CPM_{experimental} - CPM_{spontaneous}}{CPM_{total} - CPM_{spontaneous}} \times 100$$

Heterotopic Heart Transplantation: Abdominal heterotopic heart transplantation was performed as previously described by Ono and Lindsey, *J. Thorac. Cardiovasc. Surg.* 7:225–229 (1969) using C56B1/6 donors and CBA recipients. Metalloporphyrin was administered intraperitoneally using various protocols. Heart allograft survival was monitored daily by direct palpation, and rejection was defined as termination of palpable cardiac contractility. Results are expressed as percentage graft survival at a given postoperative period. Statistical analysis was performed with the Mann-Whitney test.

Results

Figure 1:
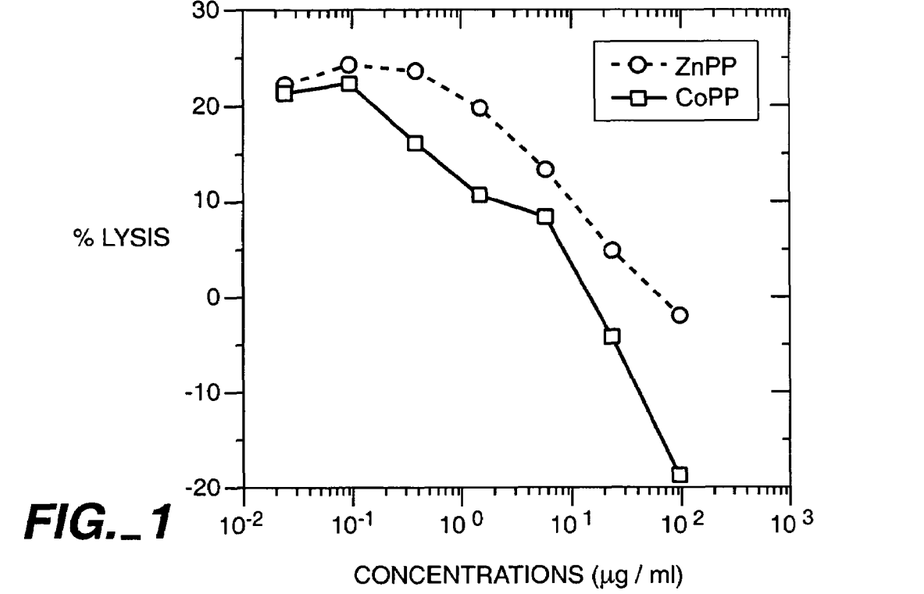
FIG. 1 is a graph of the inhibition of target cell lysis by treatment with metalloprotoporphyrins. T-cell mediated cell lysis was evaluated in the presence of varying amounts of Zn- and Co-protoporphyrin in a four hour chromium release assay.
Figure 2:
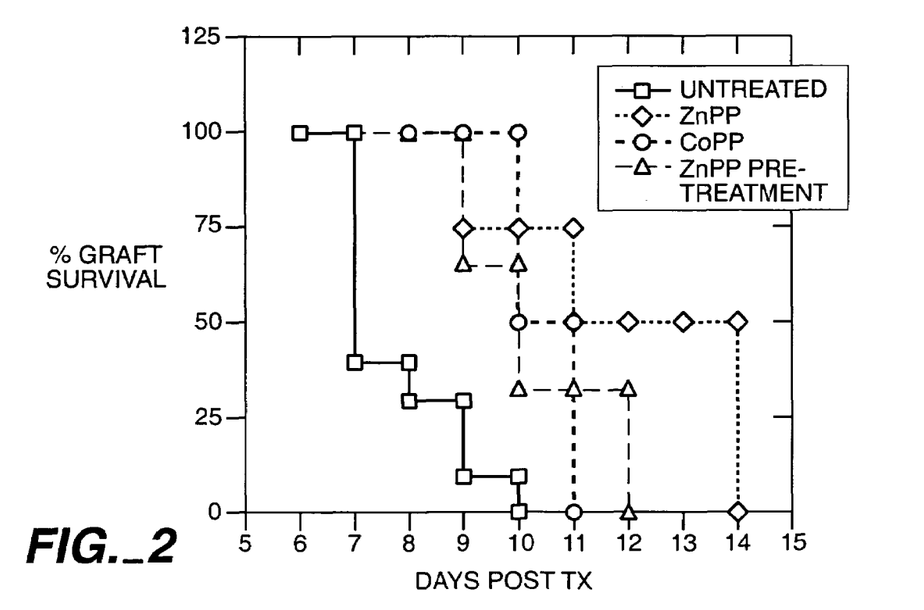
FIG. 2 is a graph showing the prolongation of heart allograft survival following metalloprotoporphyrin therapy. CBA recipients of C57B1/6 heart allografts were either untreated or treated as follows: Zn-protoporphyrin group (n=4); Zn-protoporphyrin was administered at 10 mg/kg/day on day −1 before transplantation and on days 1–9 post transplantation. Co-protoporphyrin group (n=4); Co-protoporphyrin was administered at 20 mg/kg/day on days 0–5 post-transplantation; Zn-protoporphyrin pretreatment group (n=3); heart donors were treated one day before transplantation with 50 mg/kg Zn-protoporphyrin.
Figure 4:
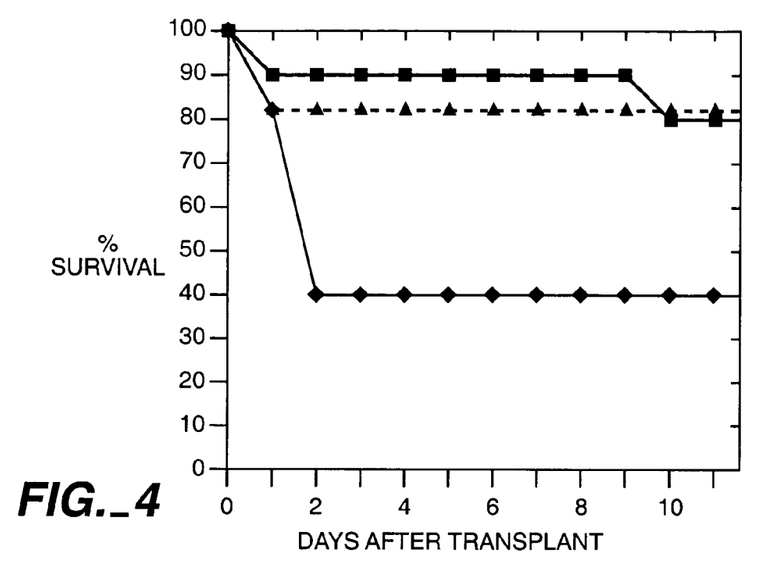
FIG. 4 shows results demonstrating prolongation of liver isograft survival. Lean Zucker rats served as recipients of liver transplants from obese Zucker donors. Donor rats were either pretreated with CoPP or Ad-HO-1 or remained untreated before liver procurement followed by 4 hours of cold ischemia. Control animal survival at 14 days was 40% (♦) versus 80% (■) and 81.8% (▲) in the CoPP and the Ad-HO-1 group, respectively (n=10–11 rats/group).
Figure 5:
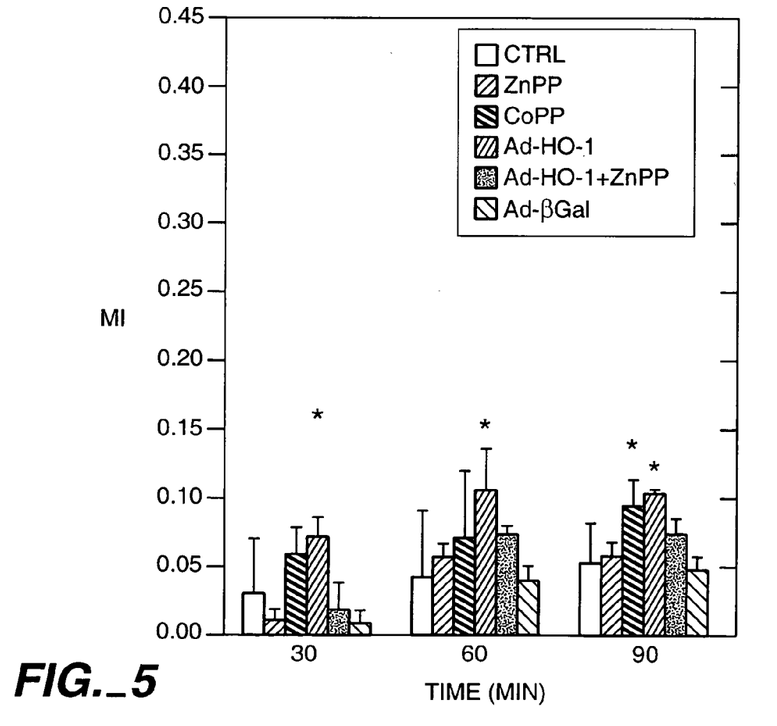
FIG. 5 shows bile production in fatty livers perfused for 2 hours on the isolated perfusion rat liver apparatus after 6 hours of cold ischemia. Animals were pretreated with metalloporphyrins, or with Ad-HO-1 gene transfer, or left untreated. Bile production at 30-minute intervals throughout the reperfusion period was significantly higher in the CoPP/Ad-HO-1 groups (*P<0.05) as compare d with untreated, ZnPP-, or Ad-β Gal—pretreated controls. These data represent the mean±SE of 4–10 independent perfusions for each group. *P<0.05 versus untreated/ZnPP-treated controls.

Zinc- and cobalt-protoporphyrin inhibit cytotoxicity in vitro. The effect of Zn- and Co-protoporphyrins on T- and NK-cell mediated cytotoxicity was evaluated in an in vitro four hour chromium release assay. Results of a representative experiment using cytotoxic T-cells are shown in FIG. 1. Similar results were observed in NK-cell assays. Addition, of protoporphyrin to the tissue culture inhibited target cell lysis in a dose dependent manner. At about 10 µg/ml target cell lysis was inhibited completely (0% lysis). At even higher concentrations, chromium release from target cells in the presence of protoporphyrins was lower than the spontaneous release observed in the absence of the compounds. These results demonstrate modulation of HO activity by metalloporphyrins results in inhibition of cytotoxicity in vitro.

Zinc- and cobalt-protoporphyrin therapy of heart allograft recipients results in prolongation of graft survival. The effect of metalloprotoporphyrins therapy on heart allograft survival was evaluated in a mouse model. CBA recipients of C57B1/6 hearts were treated following transplantation with several doses of Zn- or Co-protoporphyrin. Compared to control animals (mean survival time=7.8±1.1) heart allograft survival was significantly prolonged to 12.0±2.4 (p=0.008) and 10.5±0.6 (p=0.004) days in Zn- or Co-protoporphyrin treated animals, respectively. Pre-treatment of heart donors one day before transplantation resulted in a prolongation of graft survival to 10.3±1.5 days (p=0.03).

It is evident from the above results, that by using metalloprotoporphyrins, one can greatly extend the survival of implants in a host. The compounds have few side effects and can be used safely with positive results.

Example 2

Heme Oxygenase-I Nucleic Acid-induced Immunomodulation

In Example 1 it is demonstrated that upregulation of heme oxygenase in donor hearts results in prolongation of heart allograft survival. To evaluate if transfection of donor hearts with a cDNA encoding heme oxygenase-I results in elevated heme oxygenase-I activity and prolonged heart allograft survival, a cDNA encoding the human heme oxygenase-I polypeptide (for the nucleic acid sequence, see nucleotides 81–944 of FIG. 3 (SEQ ID NO:1)) is cloned into a plasmid expression vector, wherein expression of the gene is under transcriptional control of the CMV promoter. Plasmid DNA is then mixed with Lipofectin reagent and diluted in a 5% glucose solution. The hearts are then excised from LEW recipients and flushed with 5% glucose solution, followed by the solution containing the DNA/liposome particles. After incubation for 10 minutes, the transfected hearts are transplanted heterotopically into ACI recipients. Allograft survival is monitored daily by direct palpation and compared with untreated grafts.

Example 3

Extended Survival of Orthotopic Liver Transplants with Adenovirus HO-I Transfected Livers Materials and Methods Animals: Genetically obese (fa/fa) male Zucker rats (220–275 g) and lean (fa/–) Zucker rats (250–300 g) were used (Harlan Sprague Dawley Inc., Indianapolis, Ind., USA). Animals were fed standard rodent chow and water ad libitum and cared for according to guidelines approved by the American Association of Laboratory Animal Care.

Synthetic metalloporphyrins: Metalloporphyrins (CoPP and ZnPP) were purchased from Porphyrin Products Inc. (Logan, Utah, USA). They were dissolved in 0.2 M NaOH, subsequently adjusted to a pH of 7.4, and diluted in 0.85% NaCl. The stock concentration of metalloporphyrins was 1 mg/mL.

Ad-HO-1 construct: A 1.0-kbp XhoI-HindIII fragment from the rat HO-1 cDNA clone pRHO-1, containing the entire coding region was cloned into plasmid pAC-CMV-pLpA. Ad-HO-1 was generated byhomologous recombination in 911 cells after cotransfection with the pAC-HO-1 plasmid and plasmid pJM17. The recombinant Ad-HO-1 clones were screened by Southern blot analysis. Ad containing the *Escherichia coli* β-galactosidase gene (Ad-β Gal) is well known in the art.

Syngeneic Orthotopic Liver Transplant (OLT) model: Syngeneic liver transplants were performed using fatty livers that were harvested from obese Zucker rats and stored for 4 hours at 4° C. in University of Wisconsin (UW) solution before being transplanted into lean Zucker recipients. OLTs were performed with revascularization without hepatic artery reconstruction. There were 2 treatment groups. In the first group, obese Zucker rats (n=10) received CoPP (5 mg/kg intraperitoneally) 24 hours before the procurement. Group 2 donors (n=11) were treated with Ad-HO-1 ($2.4 \times 10^9$ pfu intravenously) 24 hours before harvest. OLT recipients were followed for survival and serum glutamic-oxaloacetic trans-aminase (sGOT) levels. Separate groups of rats (n=2/group) were sacrificed at 1, 7, 14, and 100 days after OLT, and liver samples were collected for H&E/immunohistology staining and Western blot analysis.

Histology and immunohistochemistry: Liver specimens were fixed in a 10% buffered formalin solution and embedded in paraffin. Sections were made at 4 µm and stained with H&E. The previously published Suzuki's criteria (Suzuki et al., *Transplantation* 55:1265–1272 (1993)), which uses neutrophil infiltration as a measure of liver injury, were modified to evaluate the histologic severity of I/R injury in the OLT model. In this classification sinusoidal congestion, hepatocyte necrosis, and ballooning degeneration are graded from 0 to 4. No necrosis, congestion or centrilobular ballooning is given a score of 0, whereas severe congestion and ballooning degeneration as well as greater than 60% lobular necrosis is given a value of 4.

OLTs were examined serially by immunohistochemistry for mononuclear cell (MNC) infiltration. Briefly, liver tissue was embedded in Tissue Tek OCT compound (Miles Inc., Elkhart, Ind., USA), snap frozen in liquid nitrogen, and stored at −70° C. Cryostat sections (5 µm) were fixed in acetone, and then endogenous peroxidase activity was inhibited with 0.3% $H_2O_2$ in PBS. Normal heat-inactivated donkey serum (10%) was used for blocking. Appropriate primary mouse Ab against rat T cells (R73) and monocytes/macrophages (ED1) (Harlan Bioproducts for Science, Indianapolis, Ind., USA) were added at optimal dilutions.

Bound primary Ab was detected using biotinylated donkey anti-mouse IgG and streptavidin peroxidase-conjugated complexes (DAKO Corp., Carpinteria, Calif., USA). The control sections were performed by replacing the primary Ab with either dilution buffer or normal mouse serum. The peroxidase reaction was developed with 3,3-diaminobenzidine tetrahydrochloride (Sigma Chemical Co., St. Louis, Mo., USA). The sections were evaluated blindly by counting the labeled cells in triplicates in 10 high-power fields.

Western blots: Protein was extracted from liver tissue samples with PBSTDS buffer (50 mM Tris, 150 mM NaCl, 0.1% SDS, 1% sodium deoxycholate, and 1% Triton X-100, pH 7.2). Proteins (30 µg/sample) in SDS-loading buffer (50 mM Tris, pH 7.6, 10% glycerol, 1% SDS) were subjected to 12% SDS-PAGE and transferred to nitrocellulose membrane (Bio-Rad Laboratories Inc., Hercules, Calif., USA). The gel was then stained with Coomassie blue to document equal protein loading. The membrane was blocked with 3% dry milk and 0.1% Tween-20 (Amersham, Arlington Heights, Ill., USA) in PBS and incubated with rabbit anti-rat HO-1 polyclonal Ab (Sangstat Corp., San Francisco, Calif., USA). The filters were washed and then incubated with horseradish peroxidase donkey anti-rabbit Ab (Amersham Life Sciences, Arlington Heights, Ill., USA). Relative quantities of HO-1 protein were determined using a densitometer (Kodak Digital Science 1D Analysis Software, Rochester, N.Y., USA) and results were expressed in absorbance units (AU).

Statistics: Results are expressed as mean±SEM. We used the Tukey-Fisher least-significant difference (LSD) criterion for judging statistical significance where P values of less than 0.05 were considered statistically significant.

Results

HO-1 overexpression prolongs OLT survival and improves hepatic function. This experiment examined whether exogenous manipulation of HO-1 expression could extend the survival of liver transplants. OLTs were performed using steatotic Zucker livers that were cold stored for 4 hours before transplant into syngeneic lean Zucker rats. The treatment groups received a single dose of CoPP or Ad-HO-1 gene transfer 24 hours before liver procurement. As shown in FIG. 6, recipients of liver isografts that were stored before transplantation in UW solution alone had a 40% survival rate at 14 days (4 out of 10). In contrast, recipients of liver isografts pretreated with CoPP showed 80% survival rate (8 out of 10). Livers pretreated with Ad-HO-1 had 81.8% survival rate at 2 weeks (9 out of 11). Indeed, 8 out of 10 lean Zucker rats engrafted with livers from CoPP-treated obese Zucker donors were still alive at well over 100 days after transplant. Prolonged survival after CoPP or Ad-HO-1 pretreatment correlated with improved OLT function as evidenced by sGOT levels. Hence, at day 1, 7, and 14 post transplant, sGOT levels (IU/L) in control untreated OLTs of 2695, 1570, and 460, respectively, were significantly higher as compared with corresponding CoPP-pretreated (1838, 477, and 198, respectively; P<0.05) or Ad-HO-1-pretreated (1628, 244, and 137, respectively; P<0.05) OLTs.

Liver histology and MNC infiltration in the OLT model. Hepatocyte damage in the OLT model was assessed by a modified Suzuki's classification, as described above. At day 1 after transplant, control untreated liver isografts showed severe disruption of lobular architecture by ballooning change, significant edema around portal areas, and moderate to severe bile duct proliferation (Suzuki score=3.33±0.58). In addition, moderate neutrophil infiltration and hepatocyte necrosis with extreme pallor that signifies glycogen depletion in the damaged hepatocytes, were prominent in this OLT group. In contrast, CoPP pretreated liver isografts at day 1 showed less neutrophil infiltration and significantly less pallor in addition to complete preservation of lobular architecture with no evidence of congestion or necrosis (score=1.33±0.70). The Ad-HO-1-pretreated isografts showed much less neutrophil infiltration as compared with untreated controls; there was no sinusoidal congestion or hepatocyte necrosis and complete preservation of lobular architecture (score 1.50±0.5). Most histologic features characteristic for ischemic pathology resolved by 14–100 days in those 40% of untreated OLT recipients that survived 2 weeks. However, unlike in the CoPP/Ad-HO-1-pretreated groups, untreated controls still showed significant bile duct proliferation.

Liver isografts from untreated obese Zucker donors showed massive MNC infiltration as early as at 24 hours (T cells: 9±3; monocytes/macrophages: 136±31). In contrast, Zucker rats pretreated with CoPP revealed significantly decreased numbers of intragraft MNC by day 1 (T cells: 2±1; monocytes/macrophages 71±12; P<0.03 and P<0.05, respectively). We found some heterogeneity in long-term liver grafts harvested at day 100. Thus, about 50% of untreated grafts showed dense infiltration by T cells and monocytes/macrophages, followed by severe hepatocellular injury; the remainder were characterized by moderate MNC infiltration and largely preserved hepatocyte architecture. In contrast, all grafts in the CoPP group showed good preservation of hepatocyte architecture and only mild MNC infiltrate.

Western analysis of HO-1 expression in the OLT model. Western blots were employed to correlate histologic findings with local HO-1 expression in liver isografts. The relative expression levels in absorbance units were analyzed by densitometer. Improved hepatic function after CoPP treatment was accompanied by enhanced HO-1 expression at day 1, 7, 14, and 100 after transplant (1.21–2.14 AU). In contrast, the corresponding liver isografts from untreated Zucker rats showed little HO-1 expression (0.09–0.85 AU).

HO-1 overexpression, as documented by Western blot analysis, improved liver function, preserved hepatocyte integrity, and decreased inflammatory MNC infiltration, with resultant prolongation of survival after transplantation. Exogenous upregulation of HO-1 prevented or significantly decreased hepatic injury in a clinically relevant and well-defined ex vivo rat fatty liver model of syngeneic OLT. Enhanced HO-1 expression improved animal survival from 40% in untreated controls to about 80% after CoPP treatment or local Ad-HO-1 gene delivery, an ultimate test for the liver function. Collectively, these results are consistent with the ability of HO-1 to protect cells from oxidative injury.

Example 4

Heme Oxygenase-I Protection from Cold Eschemia/Reperfusion (I/R) Injury

Materials and Methods

Animals, metalloporphyrins, and adenovirus constructs are described in Example 3. Ex vivo cold ischemia model: Genetically obese Zucker rats underwent ether anesthesia and systemic heparinization. After skeletonization of the liver, the portal vein, bile duct, and inferior vena cava were cannulated, and the liver was flushed with 10 mL of University of Wisconsin (UW) solution. Control livers from untreated obese Zucker rats were stored for 6 hours at 4° C. in UW solution (n=6). There were 4 treatment groups. Group 1 animals received CoPP, the HO-1 inducer (5 mg/kg intraperitoneally) 24 hours before liver harvest (n=6). Group 2 rats were infused with Ad-HO-1 or Ad-β Gal (2.4×10$^9$ plaque-forming units (pfu) intraperitoneally) 24 to 48 hours before the procurement (n=4–10). Group 3 donors were treated with Ad-HO-1 (2.4×10$^9$ pfu intravenously) at day-2, followed 1 day later by infusion of ZnPP (20 mg/kg intraperitoneally), the HO-1 inhibitor (n=4). Group 4 rats received ZnPP alone (20 mg/kg intraperitoneally) at 24 hours before harvest (n=4). All livers were procured at day 0, stored for 6 hours at 4° C. in UW solution, and then perfused on an isolated perfusion rat liver apparatus, as described. The Zucker livers were perfused ex vivo for 2 hours while temperature, pH, and inflow pressure were kept constant. Portal vein blood flow and pressure were recorded every 15 minutes, whereas bile output was monitored every 30 minutes. Portal vein blood flow was adjusted to maintain portal pressures of 13 to 18 cm $H_2O$. Blood was collected at 30-minute intervals and serum glutamic-oxaloacetic transaminase (sGOT) levels were measured using an autoanalyzer from ANTECH Diagnostics (Irvine, Calif., USA). Following 2 hours of perfusion, a portion of the liver was snap-frozen for mRNA extraction and Western blot analysis of HO-1 expression; the remaining tissue samples were fixed in formalin for hematoxylin and eosin (H&E) staining.

Histology and immunohistochemistry: Liver specimens were fixed in a 10% buffered formalin solution and embedded in paraffin. Sections were made at 4 μm and stained with H&E. The histologic severity of I/R injury in the ex vivo perfusion model was graded using International Banff Criteria. Using these criteria, lobular disarray and ballooning changes are graded from 1 to 4, where no change is given a score of 1 and severe disarray or ballooning changes is given a score of 4.

Western blots were performed as described in Example 3.

Statistics: Results are expressed as mean±SEM. Statistical comparisons between the groups in the ex vivo perfusion model were performed using repeated measure ANOVA. We used the Tukey-Fisher least-significant difference (LSD) criterion for judging statistical significance where P values of less than 0.05 were considered statistically significant.

Results

The effects of HO-1-inducing agents in the ex vivo steatotic rat liver cold ischemia model followed by reperfusion: To test that overexpression of HO-1 decreases I/R-mediated hepatocyte injury, we monitored portal vein blood flow, bile production, and sGOT levels in livers from obese Zucker rats that were either untreated or pretreated with HO-1-inducing agents and then perfused for 2 hours on the isolated perfusion rat liver apparatus.

Pretreatment of Zucker rats with synthetic metalloporphyrin CoPP or Ad-HO-1 gene transfer exerted equally protective effects against liver I/R injury. Both modalities significantly improved portal blood flow throughout the 2-hour reperfusion period, as compared with untreated controls (P=0.0001). In addition, both CoPP and Ad-HO-1 significantly increased bile production (P<0.05), as compared with controls. The I/R-induced hepatocyte injury measured by sGOT release was also markedly reduced in the CoPP/Ad-HO-1 treatment groups as compared with controls. For instance, at 60 minutes of reperfusion, sGOT concentrations were 53.3±8.23 IU/L and 68.8±10.1 IU/L in the CoPP and Ad-HO-1 groups, respectively, versus 102±8.23 IU/L in untreated controls (P<0.02). In contrast, Ad-β Gal gene transfer did not affect the extent of I/R insult suffered otherwise by steatotic rat livers ZnPP abrogates the beneficial effects of HO-1 upon hepatic I/R injury. To determine if the amelioration of hepatocyte injury in this I/R model was indeed mediated by an increase in HO-1 activity, prospective liver donors were pretreated with ZnPP, a potent HO-1 inhibitor. Unlike in the CoPP group, livers procured from obese Zucker rats pretreated with ZnPP alone exhibited diminished portal blood flow and bile production, effects that were accompanied by augmented hepatocyte injury comparable with otherwise untreated fatty controls. Interestingly, infusion of ZnPP abolished Ad-HO-1-mediated protective effects upon I/R injury in steatotic rat livers. Therefore, portal blood flow and bile production were significantly (P<0.05) decreased, and hepatocyte function became impaired after adjunctive ZnPP treatment, as compared with Ad-HO-1 monotherapy.

Liver histology in the ex vivo cold ischemia model followed by reperfusion.: The I/R-induced hepatocyte injury in the ex vivo model was graded using Banff's criteria. In the untreated fatty Zucker group, there was severe disruption of lobular architecture with marked zone 3 ballooning change, focally associated with hepatocyte necrosis (Banff's score=3.0±0.63). The ZnPP-treated livers showed somewhat less lobular ballooning changes, but more sinusoidal and vascular congestion (score=2.86±0.12). In marked contrast, CoPP-treated livers showed complete preservation of the lobular architecture with no signs of hepatocyte necrosis (score=1.21±0.39). Similarly, livers transduced with Ad-HO-1 revealed focal areas of mild vacuolar degeneration with minimal hepatocyte necrosis (score=1.68±0.51). However, livers procured from animals treated with Ad-HO-1 plus ZNPP were characterized by severe disruption of the lobular architecture, similar to the control untreated group, with profound zone 3 ballooning change accompanied by confluent areas of hepatocyte necrosis (score=2.74±0.26). Livers treated with Ad-β Gal revealed less necrosis compared with the untreated group, but had severe architectural disruption and vascular congestion (score=3.0±1.41).

Western analysis of HO-1 expression in the ex vivo I/R injury model: Western analysis was used to evaluate HO-1 expression in liver samples following cold ischemia at the completion of 2-hour perfusion period. The relative expression levels of HO-1 protein in AU were analyzed by densitometer. Preservation of hepatic function after CoPP pretreatment or Ad-HO-1 gene transfer was accompanied by enhanced HO-1 expression (2.46 and 2.12 AU, respectively). In contrast, HO-1 was diminished after adjunctive ZnPP infusion (1.18 AU) and virtually undetectable in untreated (0.11 AU) and ZnPP-pretreated (0.12 AU) controls.

To test that stress-induced upregulation of HO-1 reduces I/R insult in steatotic rat livers, we have chosen 2 distinct HO-1-inducing approaches. First, donor rats were pretreated with CoPP (5 mg/kg intraperitoneally), a regimen that increases HO-1 protein levels in rat livers by 250% in a rat sandwich ELISA. Second, because infusion of CoPP in high doses may modulate other heme enzymes such as nitric oxide synthase (NOS) and guanylate cyclase, we have also used Ad-based gene delivery to provide "proof of principle" and to selectively upregulate HO-1 expression in prospective liver donors. Western blot analysis confirmed increased HO-1 protein expression in the ex vivo I/R model using Ad-HO-1-transduced rat steatotic livers.

The beneficial effects in the ex vivo I/R-injury model were reflected by the ability of exogenously upregulated HO-1 to improve portal vein blood flow, increase bile production, and depress sGOT levels, all well-accepted parameters of hepatic function. Portal blood flow is mostly affected by resistance in the graft caused by lobular ballooning, hepatocyte swelling, and sinusoidal congestion. In this ex vivo perfusion model, the improved portal venous blood flow represents less hepatocyte injury and lobular disarray in the liver rather than the endothelium-dependant vasodilatory effects of carbon monoxide. Collectively, these results are consistent with the ability of HO-1 to protect cells from oxidative injury.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. A method for increasing the heme oxygenase level in cells of an organ transplant, comprising:

contacting cells of an organ transplant with a viral vector encoding a polypeptide having heme oxygenase activity, wherein said viral vector comprises a nucleic acid having at least 80% sequence identity to nucleotides 81–944 of the human heme oxygenase-I nucleic acid sequence of SEQ ID NO:1, whereby the heme oxygenase level is increased.

2. The method of claim 1, wherein said nucleic acid comprises nucleotides 81–944 of the human heme oxygenase-I nucleic acid sequence of SEQ ID NO:1.

3. The method of claim 1, wherein said contacting is ex vivo.

4. The method of claim 1, wherein said contacting is in vivo.

5. The method of claim 1, wherein said organ transplant is an allograft.

6. The method of claim 5, wherein said allograft is a heart.

7. The method of claim 5, wherein said allograft is a liver.

8. The method of claim 5, wherein said allograft is a kidney.

9. The method of claim 1, wherein said contacting is prior to transplantation of said organ.

10. The method of claim 1, wherein said contacting is subsequent to transplantation of said organ.

11. The method of claim 1, wherein said contacting is by direct injection of said viral vector into said organ transplant.

12. A method for increasing the heme oxygenase level in cells of an organ transplant, comprising:

contacting cells of an organ transplant with an adenoviral vector comprising a nucleic acid encoding a polypeptide with at least 80% amino acid sequence identity with the human heme oxygenase-I encoded by nucleotides 81–944 of the nucleic acid sequence of SEQ ID NO:1, wherein said polypeptide has heme-oxygenase activity, and whereby the level of heme oxygenase is increased.

13. The method of claim 12, wherein said polypeptide comprises human heme oxygenase encoded by nucleotides 81–944 of the nucleic acid of SEQ ID NO:1.

14. The method of claim 12, wherein said contacting is ex vivo.

15. The method of claim 12, wherein said contacting is in vivo.

16. The method of claim 12, wherein said organ transplant is an allograft.

17. The method of claim 16, wherein said allograft is a heart.

18. The method of claim 16, wherein said allograft is a liver.

19. The method of claim 16, wherein said allograft is a kidney.

20. The method of claim 12, wherein said contacting is prior to transplantation of said organ.

21. The method of claim 12, wherein said contacting is subsequent to transplantation of said organ.

22. The method of claim 12, wherein said contacting is by direct injection of said adenoviral vector into said organ.

* * * * *

SEQUENCE LISTING

```
<160> NUMBER OF SEQ ID NOS: 1

<210> SEQ ID NO 1
<211> LENGTH: 1550
<212> TYPE: DNA
<213> ORGANISM: Homo sapiens

<400> SEQUENCE: 1
tcaacgcctg cctccctcg agcgtcctca gcgcagccgc cgcccgcgga gccagcacga      60
acgagcccag caccggccgg atggagcgtc cgcaacccga cagcatgccc caggatttgt     120
cagaggccct gaaggaggcc accaaggagg tgcacaccca ggcagagaat gctgagttca    180
tgaggaactt tcagaagggc caggtgaccc gagacgcgtt caagctggtg atggcctccc    240
tgtaccacat ctatgtggcc ctggaggagg agattgagcg caacaaggag agcccagtct    300
tcgcccctgt ctacttccca gaagagctgc accgcaaggc tgccctggag caggacctgg    360
ccttctggta cgggccccgc tggcaggagg tcatcccta cacaccagcc atgcagcgct    420
atgtgaagcg gctccacgag gtggggcgca cagagcccga gctgctggtg gcccacgcct    480
acacccgcta cctgggtgac ctgtctgggg gccaggtgct caaaaagatt gcccagaaag    540
ccctggacct gcccagctct ggcgagggcc tggccttctt caccttcccc aacattgcca    600
gtgccaccaa gttcaagcag ctctaccgct cccgcatgaa ctccctggag atgactcccg    660
cagtcaggca gagggtgata gaagaggcca agactgcgtt cctgctcaac atccagctct   720
ttgaggagtt gcaggagctg ctgacccatg acaccaagga ccagagcccc tcacgggcac   780
cagggcttcg ccagcgggcc agcaacaaag tgcaagattc tgccccgtg gagactccca    840 gagggaagcc cccactcaac acccgctccc aggctccgct tctccgatgg gtccttacac    900
tcagctttct ggtggcgaca gttgctgtag ggctttatgc catgtgaatg caggcatgct    960
ggctcccagg gccatgaact ttgtccggtg gaaggccttc tttctagaga gggaattctc   1020
ttggctggct tccttaccgt gggcactgaa ggctttcagg gcctccagcc ctctcactgt   1080
gtccctctct ctggaaagga ggaaggagcc tatggcatct tccccaacga aaagcacatc   1140
caggcaatgg cctaaacttc agaggggggcg aaggggtcag ccctgccctt cagcatcctc  1200
agttcctgca gcagagcctg gaagacaccc taatgtggca gctgtctcaa acctccaaaa   1260
gccctgagtt tcaagtatcc ttgttgacac ggccatgacc actttccccg tgggccatgg   1320
caatttttac acaaacctga aaagatgttg tgtcttgtgt ttttgtctta tttttgttgg   1380
agccactctg ttcctggctc agcctcaaat gcagtatttt tgttgtgttc tgttgttttt   1440
atagcagggt tggggtggtt tttgagccat gcgtgggtgg ggagggaggt gtttaacggc   1500
actgtggcct tggtctaact tttgtgtgaa ataataaaca acattgtctg                1550
```